Figure 1:
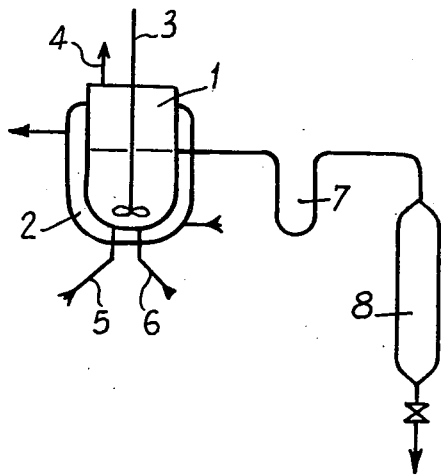

United States Patent [19]

Michel et al.

[11] 4,211,700

[45] Jul. 8, 1980

[54] PROCESS FOR THE PREPARATION OF LACTAMES THROUGH OXIME ISOMERIZATION

[75] Inventors: Jean-Claude Michel, Orthez; Philippe Potin, Billere, both of France

[73] Assignee: Ato Chimie, Courbevoie, France

[21] Appl. No.: 12,495

[22] Filed: Feb. 15, 1979

[30] Foreign Application Priority Data

Feb. 17, 1978 [FR] France ................................. 78 04571

[51] Int. Cl.$^2$ ............................................ C07D 201/04
[52] U.S. Cl. ............................. 260/239.3 A; 546/243; 260/326.5 FN
[58] Field of Search ............... 260/239.3 A, 326.5 FN; 546/243

[56] References Cited

U.S. PATENT DOCUMENTS

| | | | |
|---|---|---|---|
| 3,060,173 | 10/1962 | Von Schick et al. | 260/239.3 A |
| 3,090,739 | 5/1963 | Ito | 260/239.3 A |
| 3,239,508 | 3/1966 | Ito et al. | 260/239.3 A |
| 3,297,684 | 1/1967 | Ito et al. | 260/239.3 A |
| 3,427,303 | 2/1969 | Genas et al. | 260/239.3 A |

*Primary Examiner*—Henry R. Jiles
*Assistant Examiner*—Robert T. Bond
*Attorney, Agent, or Firm*—Bacon & Thomas

[57] ABSTRACT

The invention relates to a process for the preparation of lactames according to the so-called "Beckmann rearrangement" which consists in isomerizing oximes in a sulfuric solution, the weight ratio percentage of sulfuric acid to the combined amount of sulfuric acid and water being raised to a value above that of the sulfuric solution feed.

8 Claims, 3 Drawing Figures

PROCESS FOR THE PREPARATION OF LACTAMES THROUGH OXIME ISOMERIZATION

The present invention is directed to a process for preparing lactames through oxime isomerization in a sulfuric solution, said reaction being called the Beckmann rearrangement, which process may be more particularly applied to sulfuric solutions of oximes obtained by photonitrozation.

It is indeed known that the acid index in the photonitrozation stage must be lower than 90% but that this index is insufficient to ensure the maximum chemical output of the rearrangement.

The aim of the invention is to overcome the drawbacks resulting from the adoption of such a compromise, by offering a method which is easy to operate as well as by considerably increasing the rearrangement reaction output and the quality of the lactames produced.

The object of the present invention is a process for preparing lactames through oxime isomerization in a sulfuric solution, said reaction being called the Beckmann rearrangement, which may be more particularly applicable to sulfuric solutions of oximes obtained by photonitrozation, wherein during the rearrangement stage the acid index of the mixture is raised to a value above that of the sulfuric solution feed.

By "acid index" of the mixture, is meant in the present description the weight ratio percentage in this mixture of $H_2SO_4$ to the combined amount of $H_2SO_4 + H_2O$, thus $H_2SO_4/(H_2SO_4 + H_2O)$.

There is no upper acid index limit to the index which it is desirable to be reached and thus, in accordance with another characteristic of the invention, it is possible to increase the acid index through the addition of sulfuric anhydride or oleum in the reaction medium. This enables the obtention of solutions containing free sulfuric anhydride but the operation shows that it is not worthwhile exceeding an index of approximately 95%, above which point the increase in output from the rearrangement reaction is low and no longer justifies the outlay which the increasing of the acid index requests.

According to another characteristic of the invention, the sulfuric acid index is increased by evaporation of part of the water contained in the reaction medium while benefitting, as evidenced by applicant, from a particular property of the sulfuric solution of the lactames. Indeed, the applicant found that the vapor pressure of the sulfuric acid-water-lactame mixture was clearly above that of the sulfuric acid-water mixture having the same value as defined above. Furthermore, the proportion of sulfuric acid in the vapor in equilibrium with the mixture containing the lactame is much lower than the vapor in equilibrium with the sulfuric acid-water simple mixture of the same value. These two properties, the increase of the vapor pressure and the reduction of the sulfuric acid concentration in the vapor, are very favorable to a partial evaporation of the water contained in the reaction medium and this especially in the field of temperatures normally used during the Beckmann rearrangement. The table below illustrates these phenomena:

TABLE 1

| | Temperature °C. | Pressure Torr | Concentration % of $H_2SO_4$ in the vapor |
|---|---|---|---|
| $H_2SO_4$ at 90.5% | 170 | 18 | 18 |
| Solution at 25% of dodecalactame in $H_2SO_4$ at 90.5% | 173 | 167 | 0.71 |

The partial evaporation of the water can particularly be obtained by bringing under more or less high vacuum the rearrangement reactor or a flash tank disposed on a circulation loop of the rearrangement reactor. The vacuum may possibly be lower when the water vapor is carried along by a dry gas, either directly in the rearrangement reactor or in the flash tank as mentioned above. Of course, it is well understood that the increase of the sulfuric acid index can simultaneously occur with the addition of sulfuric anhydride or oleum and by water evaporation.

Whatever the method used, the initial concentrations of the reacting products are chosen such that the concentration of lactame in the final reaction medium is comprised between 5 and 50%, and preferably comprised between 15 and 35% by weight.

The temperatures at which the reaction occurs are comprised between 80° and 200° C. and preferably between 120° and 180° C. and the contact times are from 0.5 to 60 minutes, and preferably from 5 to 20 minutes.

This method may be applied to the isomerization of $C_4$ to $C_{12}$ oximes.

Figure 3:
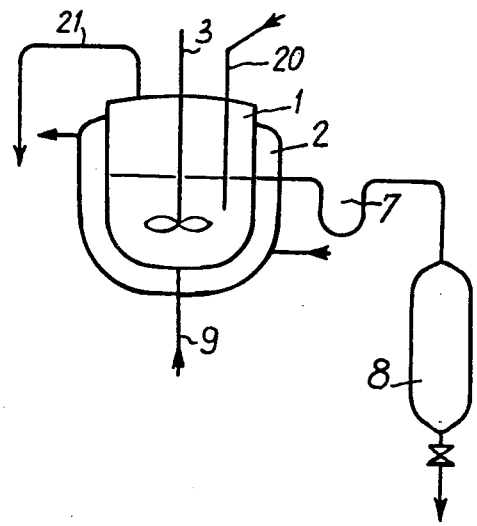
Figure 2:
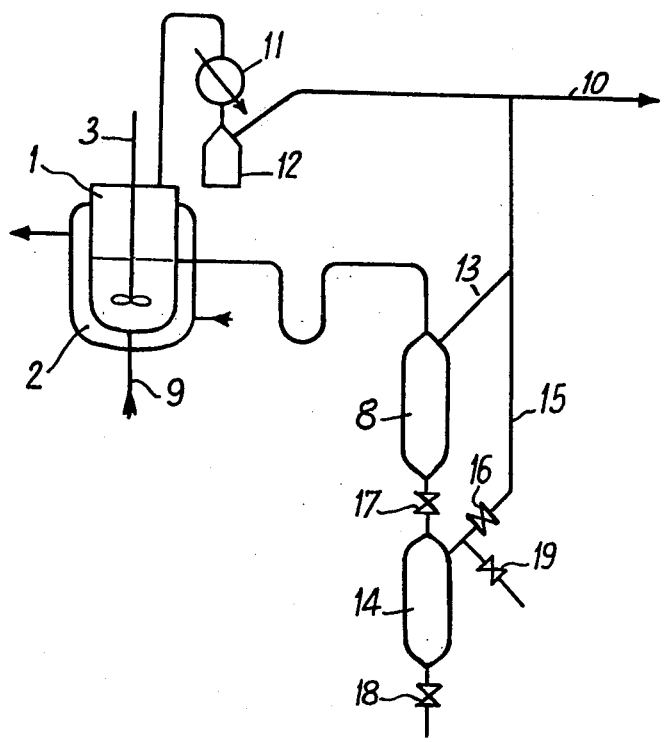

The invention will be better understood with reference to the description hereunder and the figures attached in which:

FIGS. 1, 2 and 3 represent installations for operations according to the invention illustrated by examples 1, 2 and 3.

EXAMPLE 1

The installation in FIG. 1 comprises a rearrangement reactor 1 heated by oil circulation in a jacket 2; said reactor is provided with a stirrer 3 and vent 4 in order that the pressure in the reactor is the atmospheric pressure. The sulfuric solution of oxime and oleum is introduced continuously through respectively conduits 5 and 6. The reactor mixture containing thus the lactames produced by the rearrangement is evacuated also continuously, through siphon 7 and is collected in reception flask 8. Table 2 hereunder gives the details of the reactor operating conditions. The sulfuric acid index and the concentrations of the cyclododecanone oxime and dodecalactame are given by weight %.

The outputs are calculated by the weight ratio of the dodelactame produced to the cyclodecanon oxime fed. The differences in flow rate between the feed and the exit result from the losses of volatile products through vent 4.

TABLE 2

| | Tests | |
|---|---|---|
| | Reference test | Reconcentrated by oleum |
| Flow rate of oxime sulfuric solution | 124 gr/mn | 115 gr/mn |
| $H_2SO_4$ index | 85.3% | 85.3% |
| cyclododecanone oxime | 30.1% | 30.1% |
| Oleum flow rate | | |

TABLE 2-continued

| | Tests | |
|---|---|---|
| | Reference test | Reconcentrated by oleum |
| at 65% | 0 | 18.33 gr/mn |
| Reactor solution flow rate | 117 gr/mn | 125 gr/mn |
| H₂SO₄ index | 83.1% | 89.5% |
| dodecalactame | 27.02% | 26.6% |
| θ°oil | 150° C. | 108.5° C. |
| θ°reactor | 149° C. | 150° C. |
| Average contact time | 13 mn 32 sec. | 13 mn 29 sec. |
| Yield | 84.4% | 96.2% |
| Quality of the final lactame — Melting point | 151.5° C. | 151.° C. |
| Bromine index | 0.30% | 0.12% |
| Permanganate index | 180 | 325 |
| Sulfuric test | 34 | 52.5 |

EXAMPLE 2

The essential part of the installation as shown in FIG. 2 resides again in the reactor 1 heated by oil circulation in a jacket 2 and provided with a stirrer 3 and a conduit 9 for the introduction of the sulfuric solution of oxime. The entire reactor is placed under reduced pressure by means of a tube 10 connected to a vacuum pump. The volatile products are re-cooled in exchanger 11 and collected in trap 12. The reactor mixture passes through siphon 7 and is collected in flash tank 8 which is subjected to the same pressure as the top of the reactor through conduit 13.

When it is desirable to recover the lactame solution from flash tank 8, flash tank 14 is subjected to reduced pressure through conduit 15, valve 16 thus being open and valves 17, 18 and 19 being closed. The opening of valve 17 allows the product to pass in the lower flash tank 14 where it is thereafter possible to recover it by means of atmospheric pressure valve 19, valves 16 and 17 being thus, of course, closed.

Table 3 hereafter gives the details of the working conditions.

TABLE 3

| | TESTS | | | |
|---|---|---|---|---|
| | Reference test | Vacuum | Reference test | Vacuum |
| Flow rate of oxime sulfuric solution | 69.7 gr/mn | 66.45 gr/mn | 73 gr/mn | 77.80 gr/mn |
| H₂SO₄ index | 87.40% | 87.40% | 87.40% | 87.40% |
| (cyclododecanone oxime) | 24.68% | 24.68% | 24.68% | 24.68% |
| Pressure | 760 torrs | 128 torrs | 760 torrs | 150 torrs |
| Reactor solution flow rate | 65.35 gr/mn | 61.60 gr/mn | 64.90 gr/mn | 60.30 gr/mn |
| H₂SO₄ index | 85.45% | 90.33% | 85.45% | 94.35% |
| dodecalactame | 23.92% | 25.04% | 24.31% | 29.40% |
| θ° oil (°C.) | 166° | 199° | 191° | 210° |
| θreactor (°C.) | 160.3° | 158.8° | 170° | 172° |
| Average contact time | 13 mn 17 sec. | 13 mn 18 sec. | 17 mn | 17 mn 20 sec. |
| Yield | 90.90% | 94.50% | 91.80% | 97.30% |
| Quality of the final lactame — Melting point | 151.3° C. | 151.4° C. | 151.° C. | 151.6° C. |
| Bromine index | 0.21 | 0.08 | 0.19 | 0.07 |
| Permanganate index | 245 | 475 | 275 | 620 |
| Sulfuric test | 37 | 48 | 41 | 58 |

TABLE 4

| | TESTS | |
|---|---|---|
| | reference test | re-concentrated |
| flow rate of sulfuric solution of oxime | 78 gr/mn | 75 gr/mn |
| H₂SO₄ index | 86.18% | 86.18% |
| (cyclododecanone oxime) | 27.6% | 27.6% |
| Nitrogen flow rate | 0 | 20 l/mn |
| Reactor solution flow rate | 71 gr/mn | 66.2 gr/mn |
| H₂SO₄ index | 84.90% | 92.46% |
| (dodecalactame) | 26.38% | 30.04% |
| θoil | 171° C. | 221° C. |
| θreactor | 167° C. | 169° C. |
| Average contact time | 16 min | 18 min |
| Yield | 87% | 96.1% |
| Quality of the final lactame — Melting point | 151.3° C. | 151.4° C. |
| Bromine index | 0.23 | 0.07 |
| Permanganate index | 155 sec. | 680 sec. |
| Sulfuric test | 39 | 57 |

EXAMPLE 3

The installation as shown according to FIG. 3 comprises equally a reactor heated by a jacket 2 and provided with a stirrer 3 and a conduit 9 for the continuous introduction of the sulfuric solution of oxime. A controlled input of nitrogen is introduced by the dip pipe 20. The exit of the gaseous mixture of volatile products-nitrogen-water is effected through vent 21. As in Example 1, the dodecalactame solution passes continuously through siphon 7 and is collected in reception balloon 8. Table 4 gives details of the working conditions.

What is claimed is:

1. A process for preparing lactames through oxime isomerization in a sulfuric solution, said reaction being called the Beckmann rearrangement, which process may be more particularly applied to sulfuric solutions of oximes obtained through photonitrozation and in which during the rearrangement stage the acid index of the mixture is raised to a level above that of the sulfuric solution feed, wherein the increase of the sulfuric acid index is effected by:
   (a) evaporating part of the water contained in the reaction medium;
   (b) adding sulfuric anhydride or oleum to the reaction medium; or
   (c) evaporating a part of the water contained in the reaction medium and adding sulfuric anhydride or oleum to the reaction medium.

2. The process according to claim 1 wherein the increase of the sulfuric acid index is effected by evaporating part of the water contained in the reaction medium.

3. Process according to claim 2, wherein the evaporation is facilitated by application of a vacuum or by stripping with an inert gas.

4. Process according to claim 3, wherein the increase in the sulfuric acid index is simultaneously effected through the addition of sulfuric anhydride or oleum and evaporation of water.

5. The process of claim 2 wherein the sulfuric acid index of the reaction mixture is from about 90% to about 95%.

6. The process of claim 5 wherein the temperature of the reaction mixture during rearrangement is between 80° to 200° centigrade.

7. The process of claim 5 wherein the final lactame concentration is between 5% and 50% by weight.

8. Process according to claim 3, 4 or 5, wherein the $C_4$ to $C_{12}$ oximes are isomerized.

* * * * *